United States Patent
Huff

[11] Patent Number: 5,908,231
[45] Date of Patent: Jun. 1, 1999

[54] LIGHT BULB FRAGRANCE DISPENSER

[75] Inventor: Rachel T. Huff, Corinth, Miss.

[73] Assignee: Huff Industries, Inc., Corinth, Miss.

[21] Appl. No.: 09/054,944

[22] Filed: Apr. 3, 1998

[51] Int. Cl.$^6$ .................................................... A61L 9/02
[52] U.S. Cl. ............................ 362/96; 362/255; 422/125
[58] Field of Search ........................... 362/96, 101, 255; 422/125, 4, 305, 306

[56] References Cited

U.S. PATENT DOCUMENTS

| | | | |
|---|---|---|---|
| 1,403,548 | 1/1922 | Gudeman | 422/125 |
| 1,535,486 | 4/1925 | Lundy | 422/125 |
| 1,920,599 | 8/1933 | Schuh | 422/125 |
| 1,966,738 | 7/1934 | Seewagen | 422/125 |
| 2,207,889 | 7/1940 | Klingman | 422/125 |
| 2,539,696 | 1/1951 | Morrison | 422/125 |
| 3,080,624 | 3/1963 | Weber | 422/125 |
| 4,184,099 | 1/1980 | Lindauer | 313/315 |
| 4,647,428 | 3/1987 | Gyulay | 422/4 |
| 4,647,433 | 3/1987 | Spector | 362/96 |

*Primary Examiner*—Thomas M. Sember
*Attorney, Agent, or Firm*—Rossi & Associates

[57] ABSTRACT

An improved fragrance dispenser of safe, simple and inexpensive design is reusable and can be utilized on a light bulb regardless of orientation of the bulb. The fragrance dispenser securely grips the light bulb at its widest point such that the light bulb may be oriented in any direction. Thus the fragrance dispenser may be used, for example, on a telescoping desk lamp or a swinging lamp where the bulb can be oriented in any direction not merely base up or base down. The fragrance dispenser is made from absorbent material that is non-combustible and reusable, such that the absorbed fragrance oil is vaporized to scent the room air with a pleasing fragrance when the light bulb is turned on and heat is generated.

6 Claims, 1 Drawing Sheet

LIGHT BULB FRAGRANCE DISPENSER

FIELD OF THE INVENTION

This invention relates in general to a device which uses the heat from a light bulb to dispense fragrance oil. More specifically, the invention provides is a simple one piece reusable unit which distributes a pleasing scent when the bulb is turned on.

BACKGROUND OF THE INVENTION

Devices which use heat from a light bulb to dispense a fragrance or other vapor are well known in the art. There are several categories of devices which distribute scent in this manner. These categories include devices which wrap a ring of an absorbent material around the neck of the bulb, adhere an impregnated pad to the bulb, rest fragrance material in a well or depression in the top of a specially designed bulb, rest on the bulb to hold a liquid, and rest a specially formed scent impregnated polyamide resin on the bulb. For example, devices which wrap a ring of an absorbent material around the neck of the bulb are disclosed in U.S. Pat. No. 1,920,599 issued to Schuh, U.S. Pat. No 2,238,476 issued to Monteith, U.S. Pat. No. 2,468,164 issued to Brewster, U.S. Pat. No. 2,539,696 issued to Morrison, and U.S. Pat. No. 2,741,812 issued to Tellier. Devices which hold or adhere an impregnated pad or cake against the bulb, are disclosed in, U.S. Pat. No. 2,372,371 issued to Eisner, U.S. Pat. No 2,435,756 issued to Schlesinger, and U.S. Patent No. 4,647,433 issued to Spector. Devices which rest fragrance material in a well or depression in the top of a specially designed bulb, are disclosed in U.S. Pat. No. 1,535,486 issued to Lundy and Ratner U.S. Pat. No 4,965,490 issued to Ratner. Devices in which an attachment to the bulb holds a liquid that is vaporized by the bulb's heat are disclosed in U.S. Pat No. 1,403,548 issued to Dugerman, U.S. Pat. No. 1,556,680 issued to Dormet, U.S. Pat. No. 4,074,111 issued to Hunter, and U.S. Pat. No. 4,647,428 Gully. U.S. Pat. No. 4,184,099 issued Lindauer et al. discloses a specially formed scent impregnated polyamide resin which rests on the bulb.

All of the know prior art scent generating devices for light bulbs have had one or more disadvantages. The devices which dispense a heated liquid create a risk of lamp breakage or liquid spillage. Also personal injury could result if the hot liquid spilled on the user. Some of the devices which around the bulb block almost of the bulb's light. Several scent producing devices are for a single use only, and when the scent is dissipated the device must be discarded.

All of the prior art inventions use gravity, a complex molded shape, or an adhesive to hold the device against the bulb. The devices which rest around the neck of or on top of the bulb are held by gravity, so they are used only when the bulb is installed either base up or base down. The devices which fit around the entire bulb using several materials such glass, foil, or plastic plus an absorbent pad are relatively complex and expensive in construction and block a significant portion of the bulb's light. The devices which are held against the bulb by an adhesive are made of several materials and are not reusable.

In view of the above, it is an object of the invention to provide an improved fragrance of safe, simple and inexpensive design that is reusable and can be utilized on a light bulb regardless of orientation of the bulb.

SUMMARY OF THE INVENTION

The invention provides an improved fragrance dispenser of safe, simple and inexpensive design that is reusable and can be utilized on a light bulb regardless of orientation of the bulb. The fragrance dispenser securely grips the light bulb at its widest point such that the light bulb may be oriented in any direction. Thus the fragrance dispenser may be used, for example, on a telescoping desk lamp or a swinging lamp where the bulb can be oriented in any direction not merely base up or base down. The fragrance dispenser is made from absorbent material that is non-combustible and reusable, such that the absorbed oil is vaporized to scent the room air with a pleasing fragrance when the light bulb is turned on and heat is generated.

In a preferred embodiment, the fragrance dispenser includes an absorbent pad having a central opening and a plurality of slits that radiate from the central opening. The slits open to form gripping portions when the fragrance dispenser is fitted over a light bulb. The absorbent pad preferably includes a scalloped outer edge, wherein the scalloped outer edge forms a plurality of petals. The plurality of petals define indentations and are preferably arranged such that the indentations are staggered with respect to the slits. In addition, outwardly extending portions of each of the petals are preferably aligned with the slits.

BRIEF DESCRIPTION OF THE DRAWINGS

The invention will now be described with reference to certain preferred embodiments thereof and the accompanying drawings, wherein.

DETAILED DESCRIPTION OF THE PREFERRED EMBODIMENTS

Figure 1:
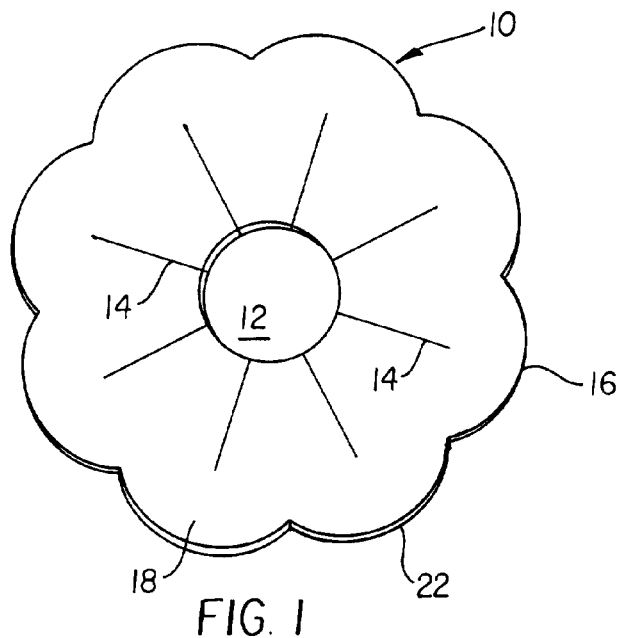
FIG. 1 is a plan view of a fragrance dispenser in accordance with the invention as a flat sheet prior to installation.

Referring now to FIG. 1, a fragrance dispenser in accordance with the invention is illustrated as including an absorbent pad 10 formed as a substantially circular ring having a central opening 12 and a plurality of slits 14 radiating therefrom. The absorbent pad 10 is preferably manufactured from Manniglas 1200 (tm), produced by Lydall Inc., Troy, N.Y., which can withstand temperatures up to 1200 degrees F. and maintains its strength even when wetted. Thus, the absorbent pad 10 can withstand the heat associated with being in direct contact with the light bulb 24 and is not subject to the health concerns posed by asbestos. Accordingly, in contrast to prior art dispensers, a separate structure is not required to hold the absorbent pad 10. The absorbent pad 10 preferably has a scalloped outer edge 16 that forms a plurality of petals 18 which define indentations 20. The petals 18 are preferably arranged such that the indentations 20 are staggered with respect to the radiating slits 14 and the almost outwardly extending portion 22 of the petals 18 are aligned with the radiating slits 14.

Figure 2:
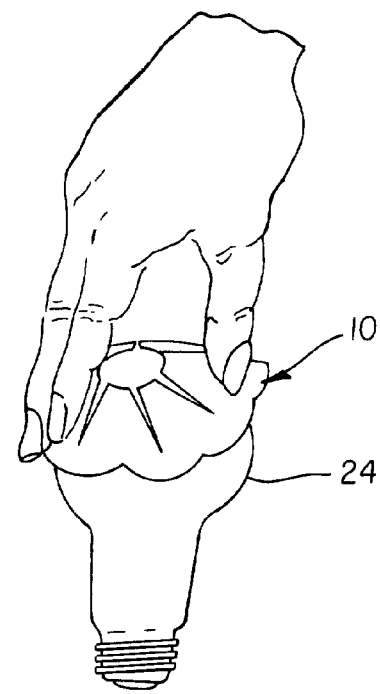
FIG. 2 is an elevational view of the fragrance dispenser being stretched over the bulb.
Figure 3:
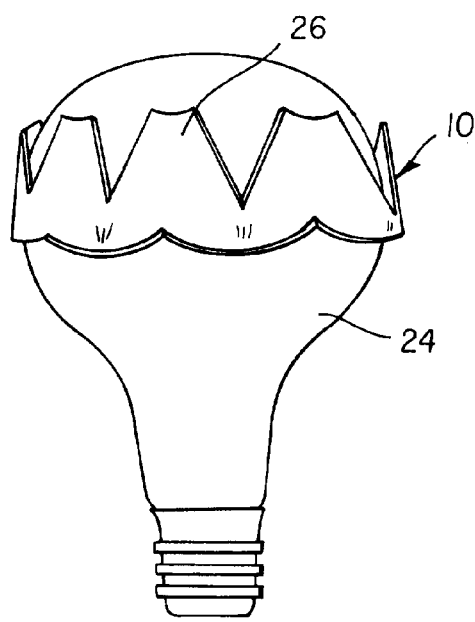
FIG. 3 is an elevational view of the fragrance dispenser in place around the bulb.

To install the fragrance dispenser, the absorbent pad 10 is fitted over the end of light bulb 24 as shown in FIG. 2 and positioned to grip the light bulb 24 securely at its widest point as shown in FIG. 3. As illustrated in FIG. 3, the radiating slits 14 open as the absorbent pad 10 is fitted over the light bulb 24 allowing the flat shape of the absorbent pad 10 to be converted to a tubular band having a plurality of gripping portions 26. The gripping portions 26 prevent the absorbent pad 10 from disengaging the light bulb 24 regardless of the orientation of the light bulb 24.

Figure 4:
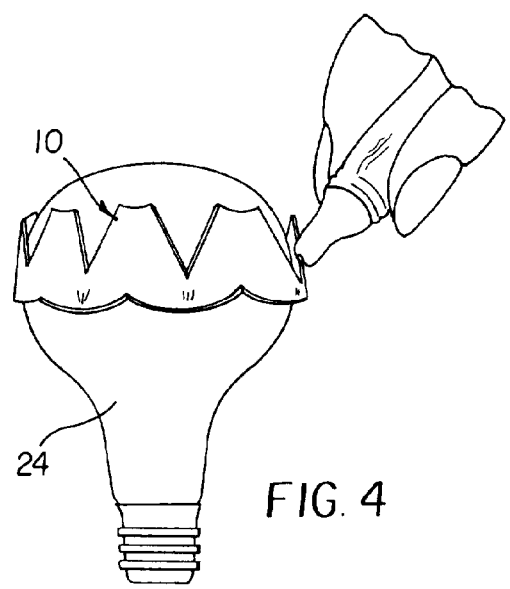
FIG. 4 is an elevational view the user putting drops of fragrance oil onto the device.

As shown in FIG. 4, drops of fragrance oil are placed on the absorbent pad 10, either after or before the absorbent pad 10 is placed on the light bulb 24. The user may use the fragrance oil of choice or mix several pleasing scents. Once the light bulb 24 is turned on the absorbed fragrance oil will be vaporized due to the heat generated by the light bulb 24. The absorbent pad 10 can be repeatedly recharged with oil for multiple uses.

The invention has been described with reference to certain preferred embodiment thereof. It will be understood, however, that modification and variations are possible within the scope of the appended claims. For example, the petals 18 and gripping portions 26 can be formed in any desired shape or configuration. Also, the absorbent pad 10 can be prescented at the time of manufacture.

What is claimed is:

1. A fragrance dispenser comprising:

an absorbent pad including a central opening and a plurality of slits that radiate from the the central opening;

wherein the slits open to form gripping portion means for gripping and retaining the absorbent pad on the light bulb for gripping a light bulb when the fragrance dispenser is fitted over the light bulbs; and wherein the gripping portion means is the sole means for retaining the absorbent pad on the light bulb.

2. A fragrance dispenser as claimed in claim 1, wherein the absorbent pad includes a scalloped outer edge.

3. A fragrance dispenser as claimed in claim 2, wherein the scalloped outer edge forms a plurality of petals.

4. A fragrance dispenser as claimed in claim 3, wherein the plurality of petals decline indentations.

5. A fragrance dispenser as claimed in claim 4, wherein the petals are arranged such that the indentations are staggered with respect to the slits.

6. A fragrance dispenser as claimed in claim 5, wherein an outwardly extending portion of each of the petals are aligned with the slits.

* * * * *